United States Patent [19]

Baker

[11] 4,017,610

[45] Apr. 12, 1977

[54] INHIBITING GROWTH OF BACTERIA, FUNGI AND ALGAE WITH A LOWER ALKYL TRI-N-OCTYL PHOSPHONIUM DIPHENYL PHOSPHATE

[75] Inventor: Don R. Baker, Orinda, Calif.

[73] Assignee: Stauffer Chemical Company, Westport, Conn.

[22] Filed: Oct. 31, 1975

[21] Appl. No.: 627,564

[52] U.S. Cl. .................................. 424/204; 21/58; 71/67

[51] Int. Cl.$^2$ ...................... A01N 9/36; A61L 1/00; A61L 13/00

[58] Field of Search ............ 21/58, 2.7 A; 424/204; 71/67; 162/161; 260/926; 252/8.5 SE, 389 A

[56] References Cited

UNITED STATES PATENTS

| | | | |
|---|---|---|---|
| 2,912,378 | 11/1959 | Bernard | 21/2.7 R |
| 3,198,733 | 8/1965 | Pera et al. | 424/301 |
| 3,364,107 | 1/1968 | Berenson et al. | 71/67 |
| 3,531,514 | 9/1970 | Redmore | 71/67 |
| 3,652,735 | 3/1972 | Hechenbleikner et al. | 424/204 |
| 3,796,595 | 3/1974 | David et al. | 162/161 |

FOREIGN PATENTS OR APPLICATIONS

| | | | |
|---|---|---|---|
| 429,293 | 7/1967 | Switzerland | 424/204 |
| 201,401 | 1966 | U.S.S.R. | 260/926 |

*Primary Examiner*—Morris O. Wolk
*Assistant Examiner*—Bradley R. Garris
*Attorney, Agent, or Firm*—Edith A. Rice

[57] ABSTRACT

The growth of fungi, algae and bacteria, including sulfate reducing bacteria, is inhibited by applying an effective amount of a lower alkyl tri-n-octyl phosphonium diphenyl phosphate.

3 Claims, No Drawings

INHIBITING GROWTH OF BACTERIA, FUNGI AND ALGAE WITH A LOWER ALKYL TRI-N-OCTYL PHOSPHONIUM DIPHENYL PHOSPHATE

DETAILED DESCRIPTION OF THE INVENTION

This invention relates to a method of inhibiting the growth of bacteria, fungi and algae by applying thereto a lower alkyl tri-n-octyl phosphonium diphenyl phosphate. These compounds can be prepared by reacting tri-n-octyl phosphine with a lower alkyl diphenyl phosphate. The term "lower alkyl" includes alkyl groups containing 1 to 4 carbon atoms.

EXAMPLE

This example illustrates the preparation of methyl tri-n-octyl phosphonium diphenyl phosphate.

To a 500 ml round bottom flask equipped with a stirrer, $N_2$ inlet, condenser, heating mantle and thermometer were added 74.1 grams (0.20 moles) of tri-n-octyl phosphine and 52.8 grams (0.20 moles) of methyl diphenyl phosphate. The reaction mixture was heated to 300° C under nitrogen for about 3 hours. The product was a pale yellow viscous fluid. The yield was 116 grams $n_D^{25} = 1.5062$.

EVALUATIONS

Methyl tri-n-octyl phosphonium diphenyl phosphate was evaluated for microbiological activity in each of the following tests.

In Vitro Agar Screening Tests

This test measures the bactericidal, fungicidal and algicidal properties of a compound when in contact with growing bacteria, fungi or algae in an artificial medium. The test is conducted by adding 20 ml portions of a suitable warm sterile agar solution into 20 × 100 mm Petri dishes. The test compound is then added at levels of 1, 5, 10 and 50 µg/ml and mixed with the warm mobile agar solution. The treated agar mixture is then allowed to come to room temperature and solidify. Cells of the chosen organism are streaked on the surface of the solidified agar and are then incubated for such lengths of time that untreated samples containing no toxicant show luxurious growth typical of the particular organism. This time varies from 24 hours to one week depending on the particular organism. The fungi are incubated at 30° C and the bacteria are incubated at 37° C. The algae are incubated at room temperature under artificial light. Nutrient agar is used as the medium in this test for the bacteria. Potato dextrose agar is used as the medium for the fungi with the exception of *Trichophyton mentagrophytes* for which Emmons agar is used. A modified Jack Meyers agar is used for the growth of the algae.

The extent of growth is noted at the end of the incubation period.

Table I shows the minimum inhibiting concentration, in µg/ml, of methyl tri-n-octyl phosphonium diphenyl phosphate required for control of the organisms listed.

Sulfate Reducing Bacteria in Vitro Test

This test measures the bactericidal properties of a compound when in contact with a sulfate reducing bacteria, specifically *Desulfovibrio desulfuricans*. The test is conducted by dissolving the test compound in acetone to give an 0.5% solution. This toxicant is added to vials containing sterile Sulfate API broth with tryptone under anaerobic conditions at such levels to give final toxicant concentrations of 1, 5, 10 and 50 µg/ml of solution. An inoculant solution of 0.5 ml of the growing organism, *Desulfovibrio desulfuricans*, is added to the vials followed by sufficient sterile distilled water to give a total of 10 ml of solution in the vials. The vials are incubated at room temperature for 3 to 5 days until untreated controls show growth of the organism as indicated by the black color development in the vials.

The minimum inhibiting concentration of methyl tri-n-octyl phosphonium diphenyl phosphate required for control of the sulfate reducing bacteria is 5 µg/ml.

Mixed Culture Sulfate Reducing Bacteria in Vitro Test

This test measures the bactericidal properties of a compound when in contact with a mixed culture of sulfate reducing bacteria isolated from an oil well. The test is conducted by dissolving the test compound in acetone to give an 0.5% solution. This toxicant is injected into vials containing sterile sulfate broth and an iron nail under anaerobic conditions at such levels to give final toxicant concentrations of 1, 5, 10 and 50 µg/ml of solution. An inoculant solution of 0.5 ml of the growing mixed culture of sulfate reducing bacteria is added to the vials followed by sufficient sterile distilled water to give a total of 10 ml of solution in the vials. The vials are incubated at room temperature for one week until controls show growth as indicated by black color development in the vials.

The minimum inhibiting concentration of methyl tri-n-octyl phosphonium diphenyl phosphate required for control of the mixed culture of sulfate reducing bacteria is 5 µg/ml. Lower alkyl tri-n-octyl phosphonium diphenyl phosphates can be applied to bacteria, fungi and/or algae to be controlled in a variety of ways at various concentrations. If desired, the active compound can be combined with suitable carriers and applied as dusts, sprays, or drenches. The amount applied will depend on the nature of the intended microbiological use.

Among the various microbiological uses of these compounds is the control of slime-forming microorganisms whose growth is a problem in aqueous systems such as lagoons, lakes, ponds, pools, cooling water systems, and pulp and paper mill systems. Such control is achieved by adding the lower alkyl tri-n-octyl phosphonium diphenyl phosphate to the particular system in a quantity adequate to control the slime-forming microorganisms.

Since the lower alkyl tri-n-octyl phosphonium diphenyl phosphates are effective against sulfate reducing bacteria they can also be used to inhibit the growth of sulfate reducing bacteria present in industrial "process water." By "process water" is meant fresh water, slightly saline water, sea water, or concentrated brines, which are utilized in or result from various industrial processes and which because of their source, mode of storage or utilization, operate as culture media for sulfate reducing bacteria. The sulfate reducing bacteria generally include the species *Desulfovibrio desulfuricans*, *Desulfovibrio orientis*, *Clostridium nigrificans*. Of these, the first is most prevalent.

Typical industrial systems employing process water are metallurgical operations employing cutting oils, latex paint preparation and storage, oil production including subsurface disposal of water withdrawn from wells and water used to repressurize wells for secondary oil recovery, packing fluids employed as "dead" layers in the casing of "multiple completion" oil well systems, and neutral drilling mud systems. In general, any process water which remains quiescent or under reduced rate of flow is subject to growth of sulfate reducing bacteria.

The harmful effects of growth of these bacteria are enormous. In oil production, for example, the bacteria cause injection well plugging and corrosion of iron and steel pipes and equipment, necessitating expensive shut-down for cleaning. Using the oil as their carbon source, the bacteria reduce sulfate ion to hydrogen sulfide ("sour gas") which in turn reacts with iron to form black particles of suspended iron sulfide. These particles clog the injection system and the once water-permeable oil-bearing formations. The bacteria are often the sole cause of pitting type corrosion of drilling equipment, either by acting as cathode depolarizers or by producing corrosive hydrogen sulfide, but more often they accelerate corrosion. See A. W. Baumgertner, "Sulfate-Reducing Bacteria . . . Their Role in Corrosion and Well Plugging," presentation at West Texas Oil Lifting Short Course, Texas Technological College, Lubbock, Texas, April 21–22, 1960.

What is claimed is:

1. A method of inhibiting the growth of sulfate-reducing bacteria which comprises applying thereto an effective amount of a lower alkyl tri-n-octyl phosphonium diphenyl phosphate.

2. The method of claim 1 wherein the bacteria are *Desulfovibrio desulfuricans*.

3. The method of claim 1 wherein the lower alkyl tri-n-octyl phosphonium diphenyl phosphate is methyl tri-n-octyl phosphonium diphenyl phosphate.

* * * * *

UNITED STATES PATENT AND TRADEMARK OFFICE
CERTIFICATE OF CORRECTION

PATENT NO. : 4,017,610

DATED : April 12, 1977

INVENTOR(S) : Don R. Baker

It is certified that error appears in the above-identified patent and that said Letters Patent are hereby corrected as shown below:

In Column 1, at line 63, please add the following table:

TABLE I

|  |  | Minimum Inhibiting Concentrations µg/ml |
|---|---|---|
| BACTERIA: | Pseudomonas aeruginosa | $>50$ |
|  | Enterobacter aerogenes | $>50$ |
|  | Bacillus cereus | $>50$ |
|  | Brevibacterium ammoniagenes | (5) |
|  | Staphylocuccus aureus | 5 |
|  | Escherichia coli | $>50$ |

UNITED STATES PATENT OFFICE
CERTIFICATE OF CORRECTION

PATENT NO. : 4,017,610
DATED : April 12, 1977
INVENTOR(S) : Don R. Baker

It is certified that error appears in the above-identified patent and that said Letters Patent are hereby corrected as shown below:

Table I continued

| | | Minimum Inhibiting Concentrations µg/ml |
|---|---|---|
| FUNGI: | Trichophyton mentagrophytes | (50) |
| | Aspergillus oryzae | (50) |
| | Aspergillus niger | >50 |
| | Aspergillus fumigatus | >50 |
| | Aspergillus flavus | >50 |
| | Penicillium italixum | (50) |
| | Penicillium expansum | >50 |
| | Rhizopus stolonifer | >50 |
| | Penicillium ochra-chloron | >50 |
| | Penicillium vermiculatum | >50 |
| | Phoma herbarum | >50 |
| | Trichoderma sp. | >50 |

UNITED STATES PATENT AND TRADEMARK OFFICE
CERTIFICATE OF CORRECTION

PATENT NO. : 4,017,610
DATED : April 12, 1977
INVENTOR(S) : Don R. Baker

It is certified that error appears in the above-identified patent and that said Letters Patent are hereby corrected as shown below:

Table I continued

|  |  | Minimum Inhibiting Concentrations $\mu g/ml$ |
|---|---|---|
| ALGAE: | <u>Chlorella pyrenoidosa</u> | (10) |
|  | <u>Scenedesmus obliquus</u> | 50 |

( ) indicates partial control at this concentration, complete control at next higher concentration $\rangle$ indicates greater than Signed and Sealed this sixteenth Day of August 1977

[SEAL]

Attest:

RUTH C. MASON
*Attesting Officer*

C. MARSHALL DANN
*Commissioner of Patents and Trademarks*